US007011848B1

(12) United States Patent
Bova

(10) Patent No.: US 7,011,848 B1
(45) Date of Patent: Mar. 14, 2006

(54) HYDROPHOBIC COMPONENT FREE SUSTAINED RELEASE NICOTINIC ACID COMPOSITIONS FOR TREATING HYPERLIPIDEMIA AND RELATED METHODS THEREFOR

(75) Inventor: David J. Bova, Hollywood, FL (US)

(73) Assignee: KOS Pharmaceuticals, Inc., Miami, FL (US)

( * ) Notice: Subject to any disclaimer, the term of this patent is extended or adjusted under 35 U.S.C. 154(b) by 0 days.

(21) Appl. No.: 09/470,603

(22) Filed: Dec. 22, 1999

Related U.S. Application Data

(63) Continuation of application No. 08/814,974, filed on Mar. 6, 1997, now Pat. No. 6,129,930, which is a continuation-in-part of application No. 08/368,378, filed on Jan. 14, 1995, now Pat. No. 6,080,428, which is a continuation-in-part of application No. 08/124,392, filed on Sep. 20, 2003, now abandoned.

(51) Int. Cl.
*A61K 9/22* (2006.01)

(52) U.S. Cl. .................. 424/468; 424/464; 424/480
(58) Field of Classification Search ............... 424/464, 424/468, 480, 465
See application file for complete search history.

(56) References Cited

U.S. PATENT DOCUMENTS

| 5,126,145 | A | * | 6/1992 | Evenstad et al. ............ 424/465 |
| 5,268,181 | A | * | 12/1993 | O'Neill et al. .............. 424/465 |
| 6,080,428 | A | * | 6/2000 | Bova ........................... 424/468 |
| 6,129,930 | A | * | 10/2000 | Bova ........................... 424/468 |

OTHER PUBLICATIONS

Expert Report of Cheryl D. Blume, Ph.D. (Jan. 27, 2004) –Subject to Protective Order.
Expert Report of Dr. Sergio Fazio (Feb. 4, 2004) [Redacted Version] –Subject to Protective Order.
Rebuttal Expert Report of Dr. Sergio Fazio (Apr. 2, 2004) –Subject to Protective Order.
Expert Report of Dr. Sergio Fazio Regarding U.S. Pat. No. 6,676,967 (Aug. 17, 2004) –Subject to Protective Order.
Expert Report of Don W. Martens (Feb. 6, 2004) [Redacted Version] –Subject to Protective Order.
Expert Report of Don W. Martens Regarding U.S. Pat. No. 6,676,967 (Aug. 20, 2004) [Redacted Version] –Subject to Protective Order.
Expert Report of Dr. Joseph R. Robinson (Feb. 5, 2004) [Redacted Version] –Subject to Protective Order.
Expert Report of Dr. Joseph R. Robinson Regarding U.S. Pat. No. 6,676,967 (Aug. 18, 2004) –Subject to Protective Order.
Rebuttal Expert Report of Thomas S. Foster, Pharm.D. (Apr. 2, 2004) –Subject to Protective Order.

Rebuttal Expert Report of Thomas S. Foster, Pharm.D. Regarding The '967 Patent (Oct. 4, 2004) –Subject to Protective Order.
Rebuttal Expert Report of James W. McGinity, Ph.D (Apr. 2, 2004) –Subject to Protective Order.
Supplemental Rebuttal Expert Report of James W. McGinity, Ph.D. (Aug. 18, 2004) –Subject to Protective Order.
Rebuttal Expert Report of James W. McGinity, Ph.D. Regarding The '967 Patent (Sep. 30, 2004) –Subject to Protective Order.
Expert Report of Mark E. McGovern, M.D. (Feb. 6, 2004) –Subject to Protective Order.
Expert Report of Mark E. McGovern, M.D. (Aug. 20, 2004) –Subject to Protective Order.
Expert Report of Frank M. Sacks, M.D. (Apr. 2, 2004) –Subject to Protective Order.
Expert Report of Frank M. Sacks, M.D. (Aug. 20, 2004) –Subject to Protective Order.
Rebuttal Expert Report of Mary Ann Tucker, Esq. (Apr. 2, 2004) –Subject to Protective Order.
Rebuttal Expert Report of Mary Ann Tucker, Esq. Regarding The '967 Patent (Oct. 1, 2004) –Subject to Protective Order.
Carl J. Lavie, et al., *Marked Benefit with Sustained–Release Niacin Therapy in Patients with Alsolated @ Very Low Levels of High–Density Lipoprotein Cholesterol and Coronary Artery Disease*, Am. J. Cardiol. 1992:69:1083–1085.
Excerpts from the 1993, 2000, and 2002 editions of the Physician's Desk Reference.
Niacin: *Double–edged Sword for Lowering Cholesterol*, Tufts University Diet & Nutritional Letter (Tufts Univ., Boston MA), Aug. 1994, vol. 12, issue 6.
Larsen, ML and Illingworth, DR, *Drug Treatment of Dyslipoproteinemia*, Med Clin N Am., 78:225–245 (1994).
Lavie, Letter to Editor, JAMA 1994; 272:513–515.
Keenan, Letter to Editor, JAMA 1994; 272:513–515.
Shields & Beckmann, Letter to Editor, JAMA 1994; 272:513–515.
Thomas N. Tozer, Clinical Pharmacokinetics Concepts and Applications (3d ed. 1995) at Chapter 9, p. 120.
Excerpts from the United States Pharmacopeia (1995).

(Continued)

*Primary Examiner*—Thurman K. Page
*Assistant Examiner*—Robert M. Joynes
(74) *Attorney, Agent, or Firm*—Karen J. Messick, Esq.

(57) ABSTRACT

An orally administered antihyperlipidemia composition according to the present invention includes from about 250 to about 3000 parts by weight of nicotinic acid, and from about 5 to about 50 parts by weight of hydroxypropyl methylcellulose. Also, a method of treating hyperlipidemia in a hyperlipidemic having a substantially periodic physiological loss of consciousness, includes the steps of forming a composition having an effective antihyperlipidemic amount of nicotinic acid and a time release sustaining amount of a swelling agent. The method also includes the step of orally administering the composition to the hyperlipidemic once per day "nocturnally," that is in the evening or at night.

12 Claims, No Drawings

OTHER PUBLICATIONS

Morgan & Capuzzi Abstract, *Safe and Effective Treatment of Dyslipidemia by Niaspan, a New Sustained–Release Niacin*, Clinical Pharmacology & Therapeutics (Feb. 1996).

Morgan & Capuzzi Article, *Treatment Effect of Niaspan, a Controlled–release Niacin, in Patients With Hypercholesterolemia: A Placebo–controlled Trial*, J. Cardiovasc. Pharmacol. Therapeut. 1(3):195–202 (Jul. 1996).

Capuzzi DM, et al., *Efficacy and Safety of An Extended–Release Niacin (Niaspan): A Long–Term Study*, Am J Cardiol. 1998;82:74U–81U.

Guyton JR, *Advances in Dyslipidemia: Discussion Session II*, Am J Cardiol, 1998: 82(12A): 85U–86U.

Knopp RH, et al., *Equivalent Efficacy of a Time–Release Form of Niacin (Niaspan) Given Once–a–Night Versus Plain Niacin in the Management of Hyperlipidemia*, Metabolism 47:1097–1104 (1998).

American Diabetes Association: *Management of Dyslipidemia in Adults with Diabetes*, Diabetes Care 21:179–182, 1998.

Elam MB, et al., *Effect of Niacin on Lipid and Lipoprotein Levels and Glycemic Control in Patients With Diabetes and Peripheral Arterial Disease*, JAMA: 2000; 284:1263–1270.

Kesala R, et al., *Niacin (N) vs. Niaspan (NS) Treatment of the Atherogenic Lipid Profile (ALP; Small, Dense LDL, HDL2, HDLc and Triglycerides) and Lp(a) in Diabetic Patients (DP)*, Diabetes 49 (suppl. 1): A268 at 1114–P (Jun. 2000).

2001 NCEP Report at VI–11, Table VI.2–3.

Wang, W. et al., *Effect of Nicotinic Acid Administration on Hepatic Very Low Density Lipoprotein–Triglyceride Production*, Am J Physiol Endocrinol Metab., 280:E540–E547 (2001).

Smith SC, et al., *AHA/ACC Guidelines for Preventing Heart Attack and Death in Patients with Atherosclerotic Cardiovascular Disease: 2001 Update*. AHA/ACC Scientific Statement, 1577–79.

Tavintharan S and Kashyap M, *The Benefits of Niacin in Atherosclerosis*, Curr Athero. Reports 2001; 3:74–82.

Meadows M., *Serious Liver Injury: Leading Reason for Drug Removals, Restrictions*, FDA Consumer Magazione, May–Jun. 2001;http://www.fda.gov/fdac/features/2001/301_liver.html.

Grundy SM, et al., *Efficacy, Safety, and Tolerability of Once–Daily Niacin for the Treatment of Dyslipidemia Associated with Type 2 Diabetes*. Arch Intern Med. 2002; 162:1568–1576.

American Diabetes Association: *Management of Dyslipidemia in Adults with Diabetes*, Diabetes Care 25:S74–S77, 2002.

Pan J, et al., *Niacin Treatment of the Atherogenic Lipid Profile and Lp(a) in Diabetes*, Diabetes, Obesity and Metabolism 4:255–261 (2002).

Pan J, et al, *Extended–Release Niacin Treatment of the Atherogenic Lipid Profile and Lipoprotein(a) in Diabetes*, Metabolism 51:1120–1127 (2002).

Meyers CD, et al., *Varying Cost and Free Nicotinic Acid Content in Over–the Counter Niacin Preparations far Dyslipidemia*, Ann Intern Med. 2003; 139:996–1002.

CDER Guidance for Industry, Bioavailability and Bioequivalence Studies for Orally Administered Drug Products –General Considerations (Mar. 2003).

American Diabetes Association: *Dyslipidemia Management in Adults with Diabetes*, Diabetes Care 27:S68–S71, 2004.

\* cited by examiner

HYDROPHOBIC COMPONENT FREE SUSTAINED RELEASE NICOTINIC ACID COMPOSITIONS FOR TREATING HYPERLIPIDEMIA AND RELATED METHODS THEREFOR

RELATED PATENT APPLICATIONS

This application for U.S. Pat. No. is a continuation of U.S. patent application Ser. No. 08/814,974, filed Mar. 6, 1997, now U.S. Pat. No. 6,129,930 which is a continuation-in-part of U.S. patent application Ser. No. 08/368,378 filed Jan. 14, 1995, now U.S. Pat. No. 6,080,428 which is a continuation-in-part of U.S. patent application Ser. No. 08/124,392 filed on Sep. 20, 1993 abandoned.

FIELD OF THE INVENTION

This invention generally relates to compositions of nicotinic acid useful for treating hyperlipidemia and methods of treating hyperlipidemia employing such compositions. More particularly, the present invention employs a composition of nicotinic acid, derivatives and mixtures thereof, and a swelling agent to form a time release sustaining composition for nocturnal or evening dosing. Specifically, the present invention employs a composition of nicotinic acid and hydroxypropyl methylcellulose to treat hyperlipidemia in a once per day oral dosage form given during the evening hours.

BACKGROUND

Nicotinic acid has been used for many years in the treatment of hyperlipidemia. This compound has long been known to exhibit the beneficial effects of reducing total cholesterol, low density lipoproteins or "LDL cholesterol", triglycerides and apolipoprotein a (Lp(a)) in the human body, while increasing desirable high density lipoproteins or "HDL cholesterol".

Nicotinic acid has normally been administered three times per day after meals. This dosing regimen is known to provide a very beneficial effect on blood lipids as discussed in Knopp et al; "Contrasting Effects of Unmodified and Time-Release Forms of Niacin on Lipoproteins in Hyperlipidemic Subjects: Clues to Mechanism of Action of Niacin"; Metabolism 34/7, 1985, page 647. The chief advantage of this profile is the ability of nicotinic acid to decrease total cholesterol, LDL cholesterol, triglycerides and Lp(a) while increasing HDL particles. While such a regimen does produce beneficial effects, cutaneous flushing and the like still often occurs in the hyperlipidemics to whom the compound is administered.

In order to avoid or reduce the cutaneous flushing, a number of materials have been suggested for administration with an effective antihyperlipidemic amount of nicotinic acid, including guar gum in U.S. Pat. No. 4,965,252, and mineral salts as disclosed in U.S. Pat. No. 5,023,245; or inorganic magnesium salts as reported in U.S. Pat. No. 4,911,917. These materials have been reported to avoid or reduce the cutaneous flushing side effect commonly associated with nicotinic acid treatment.

Another method of avoiding or reducing the side effects associated with immediate release niacin is the use of sustained release formulations. Sustained release formulations are designed to slowly release the compound from the tablet or capsule. The slow drug release reduces and prolongs blood levels of drug and thus minimizes the side effects. Sustained release formulations of niacin have been developed, such as Nicobid™ capsules (Rhone-Poulenc Rorer), Endur-acin™ (Innovite Corporation) and Pat. No. 5,126,145 which describes a sustained release niacin formulation containing two different types of hydroxypropyl methylcellulose and a hydrophobic component.

Studies in hyperlipidemic patients have been conducted with a number of sustained release niacin products. These studies have demonstrated that the sustained release products do not have the same advantageous lipid altering effects as immediate release niacin, and in fact often have a worse side effect profile compared to the immediate release product. The major disadvantage of the sustained release formulations, as can be seen in Knopp et al., 1985, is the significantly lower reduction in triglycerides (−2% for the sustained release versus −38% for the immediate release) and lower increase in HDL cholesterol, represented as $HDL_2$ particles which are known by the art to be most beneficial, (−5% for the sustained release versus +37% for the immediate release).

Additionally, sustained release niacin formulations have been noted as causing in, greater incidences of liver toxicity as described in Henken et al (Am J Med 91:1991 1991) and Dalton et al (Am J Med 93: 102 1992). There is also great concern regarding the potential of these formulations in disrupting glucose metabolism and uric acid levels.

In a recent edition of the JOURNAL OF THE AMERICAN MEDICAL ASSOCIATION (JAMA), an article appeared which presented research results investigating the liver toxicity problems associated with a sustained release form of nicotinic acid. "A Comparison of the Efficacy and Toxic Effects of Sustained- vs. Immediate-Release Niacin Hypercholesterolemic Patients", McKenney et al., JAMA, Vol. 271, No. 9, Mar. 2, 1994, page 672. The article presented a study of twenty-three patients. Of that number, 18 or 78 percent were forced to withdraw because liver function tests (LFTs) increased indicating potential liver damage. The conclusion of the authors of that article was that the sustained release form of niacin "should be restricted from use."

A similar conclusion was reached in an article authored by representatives of the Food and Drug Administration and entitled "Hepatic Toxicity of Unmodified and Time-Release Preparations of Niacin", Rader, et al., THE AMERICAN JOURNAL OF MEDICINE, Vol. 92, January 1992, page 77. Because of these studies and similar conclusions drawn by other health care professionals, the sustained release forms of niacin have experienced limited utilization.

Therefore, it can be seen from the scientific literature that there is a need for development of a sustained release niacin formulation and a method of delivering said formulation which would provide hyperlipidemic patients with "balanced lipid alteration", i.e. reductions in total cholesterol, LDL cholesterol, triglycerides and Lp(a) as well as increases in HDL particles, with an acceptable safety profile, especially as regards liver toxicity and effects on glucose metabolism and uric acid levels.

SUMMARY OF THE INVENTION

In brief, the present invention alleviates and overcomes certain of the above-identified problems and shortcomings of the present state of nicotinic acid therapy through the discovery of novel nicotinic acid formulations and methods of treatment.

It is therefore, an object of the present invention to provide a composition of nicotinic acid or any compound which is metabolized by the body to form nicotinic acid for treating hyperlipidemia.

It is another object of the present invention to provide a composition as above, which has a time release sustaining characteristic.

It is yet another object of the present invention to provide a method for employing a composition as above, for treating hyperlipidemia, which results in little or no liver damage.

At least one or more of the foregoing objects, together with the advantages thereof over the known art relating to the treatment of hyperlipidemia, which shall become apparent from the specification which follows, are accomplished by the invention as hereinafter described and claimed.

In general the present invention provides an improved antihyperlipidemia composition of the oral type employing an effective antihyperlipidemic amount of nicotinic acid, wherein the improvement comprises compounding the nicotinic acid with from about 5% to about 50% parts by weight of hydroxypropyl methylcellulose per hundred parts by weight of tablet or formulation.

present invention also provides an orally administered antihyperlipidemia composition which comprises from about 30% to about 90% parts by weight of nicotinic acid; and, from about 5% to about 50% parts by weight of hydroxypropyl methylcellulose.

The present invention also includes a method of treating hyperlipidemia in a hyperlipidemic. The method comprises the steps of forming a composition which comprises an effective antihyperlipidemic amount of nicotinic acid and an amount of excipients to provide sustained release of drug. The method also includes the step of orally administering the composition to the hyperlipidemic nocturnally.

A method of treating hyperlipidemia in a hyperlipidemic according to the invention, comprises dosing the hyperlipidemic with an effective antihyperlipidemic amount of nicotinic acid or compound metabolized to nicotinic acid by the body. The dose is given once per day in the evening or at night, combined with a pharmaceutically acceptable carrier to produce a significant reduction in total and LDL cholesterol as well as a significant reduction in triglycerides and Lp(a), with a significant increase in HDL cholesterol.

The above features and advantages of the present invention will be better understood with reference to the following detailed description and examples. It should also be understood that the particular methods and formulations illustrating the present invention are exemplary only and not to be regarded as limitations of the present invention.

DETAILED DESCRIPTION OF THE INVENTION

By way of illustrating and providing a more complete appreciation of the present invention and many of the attendant advantages thereof, the following detailed description and examples are given concerning the novel methods and formulations.

The present invention employs nicotinic acid or a compound other than nicotinic acid itself which the body metabolizes into nicotinic acid, thus producing the same effect as described herein. The other compounds specifically include, but are not limited to the following: nicotinyl alcohol tartrate, d-glucitol hexanicotinate, aluminum nicotinate, niceritrol and d,1-alpha-tocopheryl nicotinate. Each such compound will be collectively referred to hereinbelow by "nicotinic acid."

As stated hereinabove, nicotinic acid has been employed in the past for the treatment of hyperlipidemia, which condition is characterized by the presence of excess fats such as cholesterol and triglycerides, in the blood stream. According to the present invention, a sustained release composition of nicotinic acid is prepared as an example.

By "sustained release" it is understood to mean a composition which when orally administered to a patient to be treated, the active ingredient will be released for absorption into the blood stream over a period of time. For example, it is preferred that in a dosage of about 1500 milligrams (hereinafter "mgs") of nicotinic acid, approximately 100 percent of the nicotinic acid will be released to the blood stream in about 4 to about 24 hours.

The specific sustained release composition according to the present invention employs an effective antihyperlipidemic amount of nicotinic acid. By "effective antihyperlipidemic amount" it is understood to mean an amount which when orally administered to a patient to be treated, will have a beneficial effect upon the physiology of the patient, to include at least some lowering of total cholesterol, LDL cholesterol, triglycerides and Lp(a) and at least some increase in HDL cholesterol in the patient's blood stream. An exemplary effective antihyperlipidemic amount of nicotinic acid would be from about 250 mgs to about 3000 mgs of nicotinic acid to be administered according to the invention as will be more fully described hereinbelow. This amount will vary dependent upon a number of variables, including the psychological needs of the patient to be treated.

Preferably, there is also included in the sustained release composition according to the present invention, a swelling agent which is compounded with the nicotinic acid, such that when the composition is orally administered to the patient, the swelling agent will swell over time in the patient's gastrointestinal tract, and release the active nicotinic acid, or a compound which produces nicotinic acid into the gastrointestinal system for absorption into the blood stream, over a period of time. As is known in the art, such swelling agents and amounts thereof, may be preselected in order to control the time release of the active ingredient. Such swelling agents include, but are not limited to, polymers such as sodium carboxymethylcellulose and ethylcellulose and waxes such as bees wax and natural materials such as gums and gelatins or mixtures of any of the above. Because the amount of the swelling agent will vary depending upon the nature of the agent, the time release needs of the patient and the like, it is preferred to employ amounts of the agent which will accomplish the objects of the invention.

An exemplary and preferred swelling agent is hydroxypropyl methylcellulose, in an amount ranging from about 5% to about 50% parts by weight per 100 parts by weight of tablet or formulation. The preferred example will ensure a sustained time release over a period of approximately 4–24 hours as demonstrated by in vitro dissolution techniques known to the art.

A binder may also be employed in the present compositions. While any known binding material is useful in the present invention, it is preferred to employ a material such as one or more of a group of polymers having the repeating unit of 1-ethenyl-2-pyrrolidinone. These polymers generally have molecular weights of between about 10,000 and 700,000, and are also known as "povidone".

Amounts of the binder material will of course, vary depending upon the nature of the binder and the amount of other ingredients of the composition. An exemplary amount of povidone in the present compositions would be from about 1% to about 5% by weight of povidone per 100 parts by weight of the total formulation.

Processing aids such as lubricants, including stearic acid, may also be employed, as is known in the art. An exemplary amount of stearic acid in the present compositions would be from about 0.5% to about 2.0% by weight per 100 parts by weight of tablet or formulation.

Examples of various embodiments of the present invention will now be further illustrated with reference to the following examples.

General Experimental

In order to demonstrate the effectiveness of the compositions and method of the present invention over known antihyperlipidemia compositions and methods heretofore known in the art, a number of substantially identical composition were prepared according to the disclosure hereinabove. The composition ingredients and amounts are listed in TABLE IA hereinbelow.

TABLE IA

Test Tablet Composition

| Ingredient | 375 mg. | 500 mg | 750 mg |
|---|---|---|---|
| Nicotinic Acid | 375.0 | 500.0 | 750.0 |
| Hyroxypropyl methylcellulose | 188.7 | 203.0 | 204.7 |
| Povidone | 12.9 | 17.2 | 25.9 |
| Stearic Acid | 5.8 | 7.3 | 9.9 |
| TOTAL | 582.4 mg | 727.5 mg | 990.5 mg |

The ingredients were compounded together to form a tablet. More specifically, Niaspan® one daily tablets in accordance with the present invention utilize a hydrophilic matrix controlled drug delivery system. This is a dynamic system composed of polymer wetting polymer hydration and polymer disintegration/dissolution. The mechanism by which drug release is controlled depends on, for example, initial polymer wetting, expansion of the gel layer, tablet erosion and niacin solubility. After initial wetting, the hydrophilic polymer starts to partially hydrate, forming a gel layer. As water permeates into the tablet increasing the thickness of the gel layer, drug diffuses out of the gel layer. As the outer layer of the tablet becomes fully hydrated it erodes. It is believed that this erosion results in additional drug release. The controlled release from this matrix delivery system can be modified depending on the type and molecular weight of hydrophilic polymer used.

A Niaspan® formulation consists of Niacin, Methocel® E10M Premium, Povidone K90 and Hystrene 5016 (stearic acid). Methocel® E10M Premium is utilized as a controlled-release agent in the Niaspan® formulation. Methocel is a partly O-methylated and O-(2-hydroxypropylated) cellulose and is available in several grades which vary in terms of viscosity and degree of substitution. Methocel is manufactured by Dow Chemical.

Povidone K90 is employed as a granulating/binding agent in a Niaspan® formulation. Povidone is a synthetic polymer consisting of linear 1-vinyl-2-pyrrolidone groups, the degree of polymerization of which results in polymers of various molecular weights, or as indicated above. It is characterized by its viscosity in aqueous solution, relative to that of water, expressed as a K-value, ranging from 10–120. Povidone K90 has an approximate molecular weight of 1,000,000. Povidone is a hygroscopic, water soluble material. Povidone K90 present in a Niaspan® formulation is manufactured by ISP (International Specialty Products). Hystrene 5016 is utilized as an external lubricant in the Niaspan® formulation. Hystrene 5016 is a mixture of stearic acid and palmitic acid. The content of stearic acid is not less than about 40.0% and the sum of the two acids is not less than about 90.0%. Hystrene 5016 is manufactured by Witco. Refer to Table IB for Niaspan® formulation details.

Qualitatively, the four tablet strength formulations are identical. The major component of each formulation is a granulated mixture of Niacin, Methocel E10M and Povidone K90. The granulation process improves compression properties.

TABLE IB

Niaspan ® Tablet Formulations

| Niaspan ® Product | 375 mg Tablets | 500 mg Tablets | 750 mg Tablets | 1000 mg Tablets |
|---|---|---|---|---|
| Formulation, %/Tablet | | | | |
| Niacin | 64.4 | 70.5 | 77.4 | 83.1 |
| methocel E10M Premium (Intragranular) | 7.4 | 8.1 | 8.9 | 9.5 |
| Povidone K90 | 2.2 | 2.4 | 2.7 | 2.9 |
| Methocel E10M Premium (Extragranular) | 25.0 | 18.0 | 10.0 | 3.5 |
| Hystrene 5016 (Strearic Acid) | 1.0 | 1.0 | 1.0 | 1.0 |
| Tablet weight, mg | 582.5 | 709.5 | 968.6 | 1203.6 |

Niaspan® formulations are presented in white caplet shape tablets. Caplet dimensions differ with respect to product strength. The 375 mg and 500 mg Niaspan® tablets are compressed with tooling measuring approximately 0.687" in length×0.281" by width. The length and width of the 750 mg and 1000 mg tooling measures approximately 0.750"×0.320". Target tablet weight and hardness dictate thickness across the four Niaspan® products. The production of the Niaspan® tablets will now be described generally as set forth below.

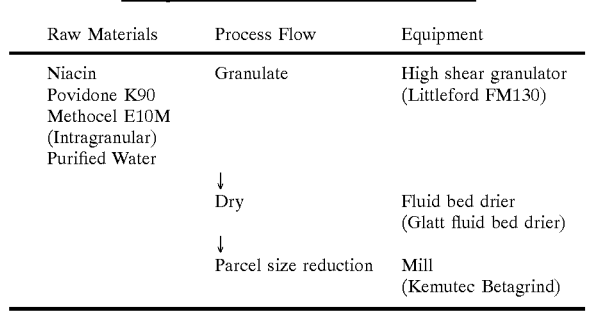

Niaspan ® Granulation Process Flow Chart

| Raw Materials | Process Flow | Equipment |
|---|---|---|
| Niacin Povidone K90 Methocel E10M (Intragranular) Purified Water | Granulate | High shear granulator (Littleford FM130) |
| | ↓ Dry | Fluid bed drier (Glatt fluid bed drier) |
| | ↓ Parcel size reduction | Mill (Kemutec Betagrind) |

Niaspan® Granulation Process Description

Niaspan® granulation raw materials are dispensed and granulated in a high shear granulator. The wet granules are sieved into a fluid bed drier and are dried. When the drying process is complete, the granules are milled. Milling ensures uniform particle size distribution throughout the Niaspan® granulation.

| Niaspan® Tablet Process Flow Chart | | |
|---|---|---|
| Raw Materials | Process Flow | Equipment |
| | Niaspan® Tablet Blend | |
| Methocel E10M (Extragranular Hystrene 5016 (Stearic acid) | Blend Milled Niaspan® granules with extragranular Methocel E10M and Hystrene 5016 ↓ | Blender (Patterson-Kelley V-Blender) |
| | Niaspan® Tablet Manufacture | |
| | Compress Niaspan® Tablet Blend | Rotary tablet press |

Niaspan® Tablet Process Description

A Niaspan® tablet blend is manufactured by blending the Niaspan® granulation, extragranular Methocel E10M and Hystrene 5016. The quantities of each Niaspan® tablet blend component will depend on the particular Niaspan® dose being manufactured (refer to Table IB). A Niaspan® tablet blend is compressed to form Niaspan® tablets. Niaspan® tablet physical properties will vary Dunedin on the particular Niaspan® dose being manufactured.

Production of Niaspan® tablets will now be discussed in greater detail. The initial stage of manufacturing is the same for all four tablet strengths of Niaspan® (375,500, 750, and 1000 mg). One batch of Niaspan granulation is comprised of four individual 40.0 kg units of granulation which are processed separately, but under like conditions. The four individual granulations are sampled and tested individually and subsequently released for blending. The base granulation is not strength specific and may be used to manufacture any tablet strength of Niaspan®.

The ingredients in the base granulation are set forth in Table IC below:

TABLE IC

| Component | Function | Quantity per kilogram granulation (kg) | % per kilogram granulation (%) | Quantity per 160.00 kg batch (kg) |
|---|---|---|---|---|
| Niacin, USP | Drug Substance | 0.87 | 87.00 | 139.20 |
| Povidone, USP | Binder | 0.03 | 3.00 | 4.80 |
| Methocel USP, E10M Premium CR Grade | Controlled-Release Agent | 0.10 | 10.00 | 16.00 |
| Purified Water, USP* | Granulation Reagent | 0.00* | 0.00* | 48.00 |
| Total | | | | 160.00 |

*Purified Water, USP is used as a granulation reagent and does not appear in the finished granulation.

Raw materials are quantitatively dispensed into appropriately labeled double polyethylene-lined containers using calibrated scales. Purified Water, USP is dispensed into an appropriate vessel from which it is later pumped during the wet-massing operation.

A Littleford FM130 granulator is charged with approximately one half of the Niacin, USP required for the process unit (~17.4 kg) followed by about 4.00 kg of Methocel, USP E10M Premium CR Grade; about 1.20 kg of Povidone, USP; and the balance of the Niacin, SP (~17.40 kg). The powder bed is dry mixed in the Littleford FM130 granulator, with choppers on, for approximately 1 minute. At the completion of the 1-minute pre-mix cycle, about 12.0±0.05 kg of Purified Water, USP are sprayed onto the powder bed at a rate of about 2.40±0.24 kg/minute. Immediately following the addition of the Purified Water, USP, the unit is granulated for about 5 minutes.

The granulated unit is discharged into double polyethylene-lined containers and then manually loaded into a Glatt bowl while being passed through a #4 mesh screen, the Glatt bowl is loaded into a Glatt TFO-60 fluid-bed drier with an inlet air temperature setting of about 70° C.±5° C. The unit is dried until a moisture level of ≦1.0% is obtained as determined using a Computrac® Moisture Analyzer, model MA5A. The dried granulation is discharged into appropriately labeled, double polyethylene-lined drums and reconciled.

The dried and reconciled granulation is passed through a Kemutec BetaGrind mill equipped with a 1.5 mm screen and running at approximately 1500 RPM. The milled granulation is collected into appropriately labeled, double polyethylene-lined drums and reconciled. The milled granulation is sampled and tested by Quality Control and released prior to further processing.

The released granulation units are charged to a Patterson-Kelley 20 ft$^3$ V-blender after which they are blended together for about 10±1 minutes and then discharged to appropriately labeled, double polyethylene-lined containers.

As stated above, Niaspan® tablets are formulated from a common granulation which is blended with appropriate quantities of Methocel, USP E10M Premium CR Grade and Stearic Acid, NF to achieve the final dosage formulation. Tables IA and IB describe the formulation for each Niaspan® tablet strength, 375 mg, 500 mg, 750 mg, and 1000 mg, respectively.

Two study groups consisting of eleven and fourteen patients each were formed. Blood samples were taken from the patients, and tested for total cholesterol, LDL cholesterol, triglycerides and HDL cholesterol to establish baseline levels from which fluctuations in these lipids could be compared. The patients were then placed upon a regimen of the above discussed tablets, totalling approximately 1500 mg of nicotinic acid, once per day before going to bed. After eight weeks of this regimen, the patients were again tested for lipid profiles. The results of the tests conducted at eight weeks, showing the changes in the lipid profiles as a percentage change from the baseline, are reported in the table hereinbelow. Positive numbers reflect percentage increases and negative numbers reflect percentage decreases in this table.

TABLE II

Patient Study Lipid Profile Data

| Pt. No. | Total-C | LDL-C | Apo B | Trigs | HDL-C | HDL-C | Lp(a) |
|---|---|---|---|---|---|---|---|
| GROUP A | | | | | | | |
| 1 | −8.2 | −12.0 | NA | −17.3 | 22.0 | NA | NA |
| 2 | −5.9 | −27.0 | NA | −28.7 | 65.0 | NA | NA |
| 3 | −15.1 | −13.0 | NA | −22.0 | −9.1 | NA | NA |
| 4 | −3.3 | −10.0 | NA | 61.6 | 3.8 | NA | NA |
| 5 | −16.5 | −17.7 | NA | −28.8 | 11.1 | NA | NA |
| 6 | −12.4 | −25.9 | NA | −42.0 | 51.6 | NA | NA |
| 7 | −24.2 | −31.4 | NA | −39.4 | 12.5 | NA | NA |
| 8 | −6.7 | −7.4 | NA | −42.4 | 18.8 | NA | NA |
| 9 | 4.5 | 1.1 | NA | 7.2 | 9.2 | NA | NA |
| 10 | 2.8 | −0.2 | NA | −2.7 | 22.9 | NA | NA |
| 11 | −13.0 | −9.4 | NA | −54.0 | 44.3 | NA | NA |
| Mean | −8.9 | −13.9 | NA | −18.9 | 23.0 | NA | NA |
| p-Value | 0.0004 | 0.0001 | | 0.0371 | 0.0068 | | |
| GROUP B | | | | | | | |
| 1 | −19.2 | −27.1 | −24.4 | −33.4 | 20.0 | 22.3 | −81.9 |
| 2 | −32.2 | −35.7 | −28.0 | −60.4 | 4.3 | 3.2 | −25.3 |
| 3 | −21.4 | −33.6 | −35.6 | −33.4 | 30.4 | 38.6 | −17.4 |
| 4 | −19.9 | −24.6 | −15.1 | −20.8 | 9.6 | 16.1 | −27.0 |
| 5 | −3.3 | −2.1 | −29.4 | −41.1 | 5.8 | 2.4 | −22.4 |
| 6 | | | PATIENT WITHDREW FROM STUDY | | | | |
| 7 | 23.1 | −32.6 | −42.6 | −58.6 | 49.2 | 68.9 | −14.3 |
| 8 | 24.8 | 34.0 | −28.4 | 5.5 | 6.5 | −6.8 | NA |
| 9 | 10.1 | 12.0 | −16.8 | −11.6 | 20.7 | −12.3 | 40.6 |
| 10 | −2.9 | 7.7 | −28.0 | −59.0 | 53.1 | 70.5 | −41.2 |
| 11 | −10.5 | −18.8 | −25.3 | −53.4 | 31.8 | 39.7 | NA |
| 12 | −20.0 | −30.8 | −30.4 | 11.7 | 21.1 | 25.0 | −28.4 |
| 13 | 17.4 | 16.8 | −17.5 | −17.5 | 51.3 | 51.9 | 38.5 |
| 14 | −9.4 | −16.6 | −32.0 | −46.9 | 52.3 | 67.6 | 17.6 |
| Mean | −8.7 | −12.8 | −32.2 | −27.2 | 25.3 | 30.1 | −17.9 |
| p-Value | 0.0002 | <0.0001 | 0.0001 | <0.001 | <0.0001 | 0.0002 | <0.0188 |
| Combined | −8.7 | −13.3 | Gp B | −26.1 | 25.3 | Gp B | Gp B |
| p-Value | 0.0002 | <0.0001 | only | <.0001 | <0.0001 | only | only |

The data reported in TABLE II shows that the LDL levels in the Group A patients had a mean decrease of −13.9% and triglyceride decrease of −18.9% HDL cholesterol levels, the beneficial cholesterol, were raised by 23.0% in this Group. Similar results were obtained with the Group B patients. These studies demonstrate that dosing the sustained release formulation during the evening hours or at night provides reductions in LDL cholesterol levels equal to immediate release niacin on a milligram per milligram basis, but superior reductions in triglyceride reductions when compared to sustained release formulations dosed during daytime hours on a milligram per milligram basis. Additionally, the increases in HDL cholesterol obtained from dosing the sustained release formulation during the evening or at night were +23.0% for one group and +25.3% for the other group. Dosing during the evening therefore provides reduction in LDL cholesterol plus significant decreases in triglycerides and increases in HDL cholesterol with once-a-day dosing.

Groups A and B were also tested for liver enzymes (AST, ALT and Alkaline Phosphatase), uric acid and fasting glucose levels at the start of the study described hereinabove (to form a baseline) and at two, four and eight week intervals. The results of these tests are listed in TABLES III-VII hereinbelow.

TABLE III

THE EFFECT OF NIASPAN ® THERAPY ON
AST (SGOT) LEVELS (U/L)
(1500 mgs dosed once-a-day at night)
(n = 28)

Weeks of Therapy With NIASPAN ™

| Pt # | Baseline | 2 Wks. | 4 Wks. | 8 Wks. | Reference Range |
|---|---|---|---|---|---|
| GROUP A | | | | | |
| 1 | 28 | 29 | 25 | 24 | 0–50 |
| 2 | 24 | 25 | 24 | 26 | 0–50 |
| 3 | 17 | 18 | 22 | 21 | 0–50 |
| 4 | 14 | 16 | 15 | 17 | 0–50 |
| 5 | 22 | NA | 32 | 52 | 0–50 |
| 6 | 21 | 17 | 17 | 14 | 0–50 |
| 7 | 17 | 17 | 14 | 18 | 0–50 |
| 8 | 20 | 21 | 22 | 22 | 0–50 |
| 9 | 16 | 16 | 17 | 20 | 0–50 |
| 10 | 18 | 21 | 21 | 25 | 0–50 |
| 11 | 21 | 21 | 22 | 21 | 0–50 |
| GROUP B | | | | | |
| 1 | 23 | 25 | 38 | 33 | 0–50 |
| 2 | 20 | 20 | 21 | 21 | 0–50 |
| 3 | 15 | 20 | 18 | 19 | 0–50 |

TABLE III-continued

THE EFFECT OF NIASPAN ® THERAPY ON
AST (SGOT) LEVELS (U/L)
(1500 mgs dosed once-a-day at night)
(n = 28)
Weeks of Therapy With NIASPAN ™

| Pt # | Baseline | 2 Wks. | 4 Wks. | 8 Wks. | Reference Range |
|---|---|---|---|---|---|
| 4 | 25 | 22 | 25 | 26 | 0–50 |
| 5 | 23 | 21 | 17 | 18 | 0–50 |
|  | PATIENT WITHDREW DUE TO FLUSHING | | | | |
| 7 | 21 | 18 | 18 | 19 | 0–50 |
| 8 | 18 | 19 | 18 | 19 | 0–50 |
| 9 | 15 | 16 | 18 | 15 | 0–50 |
| 10 | 16 | 15 | 19 | 28 | 0–50 |
| 11 | 20 | 22 | 24 | 28 | 0–50 |
| 12 | 23 | 25 | 28 | 22 | 0–50 |
| 13 | 20 | 15 | 20 | 19 | 0–50 |
| 14 | 18 | 25 | 20 | 18 | 0–50 |
| Combined Mean | 19.8 | 20.4 | 20.8 | 21.1 | |
| Change From Baseline | | +3.0% | +5.1% | +6.6% | |

Level of Significance: p = 0.4141

TABLE IV

THE EFFECT OF NIASPAN ® THERAPY ON
ALT (SGPT) LEVELS (U/L)
(1500 mgs dosed once-a-day at night)
(n = 28)
Weeks of Therapy With NIASPAN ®

| Pt # | Baseline | 2 Wks. | 4 Wks. | 8 Wks. | Reference Range |
|---|---|---|---|---|---|
| GROUP A | | | | | |
| 1 | 32 | 28 | 39 | 30 | 0–55 |
| 2 | 24 | 25 | 23 | 26 | 0–55 |
| 3 | 18 | 23 | 30 | 30 | 0–55 |
| 4 | 7 | 13 | 14 | 14 | 0–55 |
| 5 | 14 | NA | 43 | 46 | 0–55 |
| 6 | 22 | 11 | 14 | 10 | 0–55 |
| 7 | 9 | 7 | 11 | 7 | 0–55 |
| 8 | 16 | 18 | 23 | 21 | 0–55 |
| 9 | 14 | 17 | 20 | 14 | 0–55 |
| 10 | 14 | 15 | 17 | 19 | 0–55 |
| 11 | 18 | 18 | 20 | 16 | 0–55 |
| GROUP B | | | | | |
| 1 | 16 | 17 | 27 | 29 | 0–55 |
| 2 | 16 | 14 | 15 | 22 | 0–55 |
| 3 | 13 | 21 | 13 | 16 | 0–55 |
| 4 | 23 | 20 | 26 | 17 | 0–55 |
| 5 | 21 | 23 | 17 | 15 | 0–55 |
| 6 | PATIENT WITHDREW DUE TO FLUSHING | | | | |
| 7 | 21 | 16 | 18 | 21 | 0–55 |
| 8 | 18 | 20 | 17 | 18 | 0–55 |
| 9 | 11 | 5 | 11 | 8 | 0–55 |
| 10 | 8 | 10 | 14 | 17 | 0–55 |
| 11 | 17 | 12 | 18 | 16 | 0–55 |
| 12 | 14 | 18 | 20 | 16 | 0–55 |
| 13 | 14 | NA | 11 | 10 | 0–55 |
| 14 | 23 | 23 | 19 | 19 | 0–55 |
| Combined Mean | 17.7 | 17.5 | 19.3 | 18.2 | |
| Change From Baseline | | −1.1% | 9.0% | +2.8% | |

Level of Significance: p = 0.3424

TABLE V

THE EFFECT OF NIASPAN ® THERAPY ON
ALKALINE PHOSPHATASE LEVELS (U/L)
(1500 mgs dosed once-a-day at night)
(n = 28)
Weeks of Therapy With NIASPAN ®

| Pt # | Baseline | 2 Wks. | 4 Wks. | 8 Wks. | Reference Range |
|---|---|---|---|---|---|
| GROUP A | | | | | |
| 1 | 52 | 56 | 57 | 55 | 20–140 |
| 2 | 103 | 100 | 89 | 102 | 20–140 |
| 3 | 54 | 45 | 53 | 51 | 20–140 |
| 4 | 70 | 68 | 71 | 91 | 20–140 |
| 5 | 77 | NA | 74 | 81 | 20–140 |
| 6 | 55 | 48 | 49 | 51 | 20–140 |
| 7 | 72 | 71 | 79 | 75 | 20–140 |
| 8 | 55 | 49 | 47 | 50 | 20–140 |
| 9 | 53 | 55 | 56 | 45 | 20–140 |
| 10 | 74 | 73 | 75 | 75 | 20–140 |
| 11 | 18 | 18 | 20 | 16 | 20–140 |
| GROUP B | | | | | |
| 1 | 73 | 67 | 89 | 95 | 20–140 |
| 2 | 82 | 64 | 72 | 71 | 20–140 |
| 3 | 73 | 69 | 72 | 82 | 20–140 |
| 4 | 37 | 36 | 37 | 38 | 20–140 |
| 5 | 65 | 53 | 54 | 61 | 20–140 |
| 6 | PATENT WITHDREW DUE TO FLUSHING | | | | |
| 7 | 64 | 58 | 58 | 58 | 20–140 |
| 8 | 79 | 78 | 65 | 73 | 20–140 |
| 9 | 94 | 92 | 103 | 93 | 20–140 |
| 10 | 69 | 67 | 70 | 65 | 20–140 |
| 11 | 59 | 67 | 63 | 72 | 20–140 |
| 12 | 65 | 59 | 59 | 63 | 20–140 |
| 13 | 64 | 68 | 66 | 64 | 20–140 |
| 14 | 72 | 61 | 59 | 64 | 20–140 |
| Combined Mean | 66.5 | 61.5 | 63.3 | 65.8 | |
| Change From Baseline | | −6.1% | −3.4% | +0.005% | |

Level of Significance: p = 0.0236

TABLE VI

THE EFFECT OF NIASPAN ® THERAPY ON
URIC ACID LEVELS (mg/dL)
(1500 mgs dosed once-a-day at night)
(n = 28)
Weeks of Therapy With NIASPAN ®

| Pt # | Baseline | 2 Wks. | 4 Wks. | 8 Wks. | Reference Range |
|---|---|---|---|---|---|
| GROUP A | | | | | |
| 1 | 5.2 | 5.0 | 4.8 | 4.3 | 4.0–8.5 |
| 2 | 4.0 | 4.6 | 4.5 | 6.2 | 2.5–7.5 |
| 3 | 6.3 | 7.0 | 6.5 | 6.2 | 4.0–8.5 |
| 4 | 3.1 | 4.6 | 4.2 | 3.8 | 2.5–7.5 |
| 5 | 3.4 | NA | 3.3 | 4.2 | 2.5–7.5 |
| 6 | 6.6 | 5.5 | 5.6 | 4.7 | 4.0–8.5 |
| 7 | 3.8 | 4.5 | 4.3 | 4.9 | 2.5–7.5 |
| 8 | 4.4 | 3.8 | 5.1 | 4.5 | 2.5–7.5 |
| 9 | 3.9 | 4.5 | 4.6 | 3.5 | 2.5–7.5 |
| 10 | 2.6 | 2.9 | 2.8 | 2.7 | 2.5–7.5 |
| 11 | 4.7 | 5.5 | 5.2 | 5.3 | 2.5–7.5 |
| GROUP B | | | | | |
| 1 | 3.7 | 4.2 | 4.7 | 3.5 | 2.5–7.5 |
| 2 | 2.8 | 3.5 | 3.6 | 2.3 | 4.0–8.5 |
| 3 | 4.2 | 5.3 | 5.5 | 5.3 | 2.5–7.5 |
| 4 | 4.7 | 3.9 | 5.1 | 3.6 | 4.0–8.5 |
| 5 | 3.7 | 4.1 | 4.1 | 3.8 | 2.5–7.5 |

TABLE VI-continued

THE EFFECT OF NIASPAN ® THERAPY ON
URIC ACID LEVELS (mg/dL)
(1500 mgs dosed once-a-day at night)
(n = 28)
Weeks of Therapy With NIASPAN ®

| Pt # | Baseline | 2 Wks. | 4 Wks. | 8 Wks. | Reference Range |
|---|---|---|---|---|---|
| 6 | PATIENT WITHDREW DUE TO FLUSHING | | | | |
| 7 | 5.8 | 6.6 | 6.6 | 6.8 | 2.5–7.5 |
| 8 | 4.7 | 4.3 | 5.4 | 5.6 | 2.5–7.5 |
| 9 | 3.7 | 4.6 | 5.1 | 3.8 | 2.5–7.5 |
| 10 | 4.2 | 5.0 | 4.4 | 8.5 | 2.5–7.5 |
| 11 | 1.9 | 3.0 | 2.8 | 5.0 | 2.5–7.5 |
| 12 | 5.6 | 5.4 | 6.2 | 5.6 | 4.0–8.5 |
| 13 | 4.2 | 4.6 | 4.6 | 5.3 | 2.5–7.5 |
| 14 | 5.5 | 5.4 | 6.1 | 5.3 | 2.5–7.5 |
| Combined Mean | 4.54 | 4.82 | 4.92 | 4.86 | *p = 0.3450 |
| Change From Baseline | | +6.2% | +8.4% | +7.0% | |

*Level of Significance: p = 0.3450

TABLE VII

THE EFFECT OF NIASPAN ® THERAPY ON
FASTING GLUCOSE LEVELS (mg/dL)
(1500 mgs dosed once-a-day at night)
(n = 28)
Weeks of Therapy With NIASPAN ®

| Pt # | Baseline | 2 Wks. | 4 Wks. | 8 Wks. | Reference Range |
|---|---|---|---|---|---|
| GROUP A | | | | | |
| 1 | 114 | 122 | 123 | 110 | 70–115 |
| 2 | 101 | 105 | 107 | 101 | 80–125 |
| 3 | 99 | 98 | 109 | 103 | 70–115 |
| 4 | 100 | 118 | 94 | 94 | 80–125 |
| 5 | 89 | NA | 82 | 103 | 80–125 |
| 6 | 97 | 103 | 94 | 107 | 70–115 |
| 7 | 85 | 107 | 100 | 94 | 80–125 |
| 8 | 98 | 107 | 103 | 101 | 80–125 |
| 9 | 97 | 97 | 100 | 110 | 80–125 |
| 10 | 94 | 101 | 111 | 97 | 70–115 |
| 11 | 102 | 103 | 95 | 95 | 80–125 |
| GROUP B | | | | | |
| 1 | 101 | 97 | 83 | 99 | 70–115 |
| 2 | 90 | 95 | 96 | 89 | 80–125 |
| 3 | 96 | 98 | 95 | 97 | 70–115 |
| 4 | 116 | 139 | 113 | 125 | 80–125 |
| 5 | 88 | 92 | 91 | 95 | 70–115 |
| 6 | PATIENT WITHDREW DUE TO FLUSHING | | | | |
| 7 | 106 | 114 | 118 | 117 | 70–115 |
| 8 | 95 | 106 | 106 | 108 | 70–115 |
| 9 | 81 | 92 | 84 | 92 | 70–115 |
| 10 | 108 | 117 | 122 | 105 | 70–115 |
| 11 | 85 | 106 | 106 | 108 | 70–115 |
| 12 | 92 | 89 | 101 | 86 | 80–125 |
| 13 | 99 | 105 | 94 | 100 | 70–125 |
| 14 | 100 | 108 | 84 | 107 | 70–125 |
| Combined Mean | 98.4 | 105.8 | 101.6 | 102.3 | |
| Change From Baseline | | +7.5% | +3.3% | +4.0% | |

Level of Significance: p = 0.0021

In order to provide a comparison between the state of the art prior to the present invention, and in order to quantify the magnitude of the improvement that the invention provides over the prior art, another study was conducted. This study included 240 patients dosed according to the present invention as described hereinabove. Compared to this group was the group of patients studied by McKenney et al., as reported hereinabove. The results of this study are reported in TABLE VIII hereinbelow.

TABLE VIII

A Comparison of Changes in Liver Function Tests

| | DOSE | | | | | | | |
|---|---|---|---|---|---|---|---|---|
| | 0 | 500 | 1000 | 1500 | 2000 | 2500 | 3000 | TOTAL |
| McKenney SR[b] Niacin[a] | | | | | | | | |
| AST | 23.8 | 27.9 | 40.4 | 36.6 | 56.5 | na | 97.0 | |
| % | — | 117 | 170 | 154 | 237 | na | 408 | |
| Invention Dosage[c] | | | | | | | | |
| AST | 24.3 | na | 23.7 | 27.5 | 26.6 | 27.6 | 27.8 | |
| % | — | na | 98 | 113 | 109 | 114 | 114 | |
| McKenney SR Niacin | | | | | | | | |
| ALT | 25.6 | 29.5 | 36.3 | 39.0 | 59.1 | na | 100.0 | |
| % | — | 115 | 142 | 152 | 231 | na | 391 | |
| Invention Dosage | | | | | | | | |
| ALT | 21.4 | na | 18.7 | 22.6 | 21.3 | 22.4 | 21.8 | |
| % | — | na | 87 | 106 | 100 | 105 | 102 | |

TABLE VIII-continued

A Comparison of Changes in Liver Function Tests

|  | DOSE | | | | | | | |
| --- | --- | --- | --- | --- | --- | --- | --- | --- |
|  | 0 | 500 | 1000 | 1500 | 2000 | 2500 | 3000 | TOTAL |
| McKenney SR Niacin | | | | | | | | |
| ALK | 95 | 95 | 106 | 105 | 136 | na | 135 | |
| % Invention Dosage | — | 100 | 112 | 111 | 143 | na | 142 | |
| ALK | 74.7 | na | 73.9 | 76.1 | 73.4 | 76.7 | 78.0 | |
| % McKemey SR Niacin | — | na | 99 | 102 | 98 | 103 | 104 | |
| Drop | — | 0 | 2 | 2 | 7 | na | 7 | 18 |
| n | — | — | — | — | — | — | — | 23 |
| % Invention Dosage | — | 0 | 9 | 9 | 30 | na | 30 | 78 |
| Drop | — | — | 0 | 0 | 0 | 0 | 0 | 0 |
| n | — | — | 26 | 67 | 97 | 35 | 15 | 240 |
| % 1 year | — | — | 0 | 0 | 0 | 0 | 0 | 0 |
| 1 year | — | — | 15 | 46 | 77 | 31 | 15 | |
|  | — | — | 58 | 69 | 79 | 89 | 100 | 77 |

[a] Dosed twice-per-day as described in "A Comparison of the Efficacy and Toxic Effects of Sustained - vs Immediate - Release Niacin in Hypercholesterolemic Patients" by McKenney et al. Journal of the American Medial Association, Mar. 2, 1994; Vol. 271, No. 9, pages 672–677.
[b] SR is "sustained release"
[c] Dosed once-per-day at night The results of the comparison of the studies reported in TABLE VIII show that the control group (the McKenney group) had 18 of 23, or 78 percent of the patients therein drop out of the test because of an increase in their respective liver function tests. The patients withdrew at the direction of the investigator. In comparison, a group of 240 patients treated according to the present invention had zero patients drop out, based upon the same criteria for withdrawal. The tests results reported above indicate that this sustained release dosage form caused no elevation in liver function tests (i.e., no liver damage), no elevations in uric acid and only a small, 7.5% increase in fasting glucose levels which in fact decreased during continued therapy.

Thus it should be evident that the compositions and method of the present invention are highly effective in controlling hyperlipidemia in hyperlipidemics, by reducing the levels of LDL cholesterol, triglyceride and Lp(a) while increasing HDL cholesterol levels. The present invention is also demonstrated not to cause elevations in liver function tests, uric acid or glucose levels for the hyperlipidemics.

Based upon the foregoing disclosure, it should now be apparent that the use of the compositions and methods described herein will carry out the objects set forth hereinabove. It is, therefore, to be understood that any variations in sustained release formulation evident fall within the scope of the claimed invention and thus, the selection of specific component elements can be determined without departing from the spirit of the invention herein disclosed and described. In particular, sustained release excipients, binders and processing aids according to the present invention are not necessarily limited to those exemplified hereinabove. Thus, the scope of the invention shall include all modifications and variations that my fall within the scope of the attached claims.

What is claimed is:

1. A method of treating hyperlipidemia in a hyperlipidemic comprising dosing the hyperlipidemic with an effective antihyperlipidemic amount of nicotinic acid or compound metabolized to nicotinic acid by the body, once per day in the evening or at night combined with pharmaceutically acceptable carriers, to produce a reduction in total and LDL cholesterol, triglycerides and Lp(a), with a significant increase in HDL cholesterol.

2. A method, as set forth in claim 1, wherein the hyperlipidemic is dosed with from about 250 parts to about 3000 parts by weight of nicotinic acid.

3. A method of claim 1, which causes minimum liver damage, uric acid increases or elevations in fasting glucose levels.

4. A method as set forth in claim 1 wherein the release rate of said nicotinic acid or compound metabolized by the body to nicotinic acid is from about 2.0% per hour to about 25% per hour.

5. A method as set forth in claim 1 wherein said nicotinic acid or compound metabolized to nicotinic acid by the body is prepared by formulating the active compound with from about 5% to about 50% parts by weight of hydroxypropyl methylcellulose per 100 parts by weight of tablet.

6. A method, as set forth in claim 1, wherein said nicotinic acid or compound metabolized to nicotinic acid by the body is dosed in he form of a sustained release formulation or tablet containing from about 1 to about 4 parts by weight of binder per 100 pats by weight of tablet.

7. A method, as set forth in claim 4, wherein said binder is a polymer having the repeating polymerization unit 1-ethenyl-2-pyrrolidone.

8. A method, as set forth in claim 1, wherein said nicotinic acid or compound metabolized to nicotinic acid by the body is dosed in the form of a sustained release formulation or tablet comprising from about 0.5 to about 2.5 parts by weight of a lubricating agent per 100 parts by weight of tablet.

9. A method, as set forth in claim 8, wherein said lubricating agent is selected from the group consisting of stearic acid and magnesium stearate.

10. A method, as set forth in claim 1, wherein the compound metabolized to nicotinic acid by the body to nicotinic acid is nicotinyl alcohol tartate.

11. A method, as set forth in claim 10, wherein the amount of nicotinyl alcohol tartrate is from about 100 milligrams to about 500 milligrams per dosage unit.

12. A method, as set forth in claim 1, wherein the compound metabolized to nicotinic acid by the body is selected from the group consisting of: d-glucitol hexanicotinate, aluminum nicotinate, and, 1-alpha-tocopheryl nicotinate.

* * * * *

UNITED STATES PATENT AND TRADEMARK OFFICE
CERTIFICATE OF CORRECTION

| | | |
|---|---|---|
| PATENT NO. | : 7,011,848 B1 | Page 1 of 1 |
| APPLICATION NO. | : 09/470603 | |
| DATED | : March 14, 2006 | |
| INVENTOR(S) | : David J. Bova | |

It is certified that error appears in the above-identified patent and that said Letters Patent is hereby corrected as shown below:

At column 2, line 34, please delete the phrase "18 or 78 percent" and insert the phrase --12 or 52 percent --.

At column 15, line 34, please delete the phrase "had 18 of 23, or 78 percent" and insert the phrase --had 12 of 23, or 52 percent--.

Signed and Sealed this

Twenty-eighth Day of November, 2006

JON W. DUDAS
*Director of the United States Patent and Trademark Office*

UNITED STATES PATENT AND TRADEMARK OFFICE
CERTIFICATE OF CORRECTION

PATENT NO. : 7,011,848 B1 Page 1 of 1
APPLICATION NO. : 09/470603
DATED : March 14, 2006
INVENTOR(S) : David J. Bova It is certified that error appears in the above-identified patent and that said Letters Patent is hereby corrected as shown below:

On the Title Page, Item [63], Related U.S. Application Data, change "Continuation of application No. 08/814,974, filed on Mar. 6, 1997, now Pat. No. 6,129,930, which is a continuation-in-part of application No. 08/368,378, filed on Jan. 14, 1995, now Pat. No. 6,080,428, which is a continuation-in-part of application No. 08/124,392, filed on Sep. 20, 1993, now abandoned" to --Continuation of application No. 08/814,974, filed on Mar. 6, 1997, now Pat. No. 6,129,930, which is a continuation-in-part of application No. 08/368,378, filed on Jan. 4, 1995, now Pat. No. 6,080,428, which is a continuation-in-part of application No. 08/124,392, filed on Sep. 20, 1993, now abandoned--

Signed and Sealed this

Third Day of August, 2010

David J. Kappos
*Director of the United States Patent and Trademark Office*